United States Patent [19]

Wiegner et al.

[11] 4,412,833

[45] Nov. 1, 1983

[54] TAMPON APPLICATOR

[75] Inventors: Georg Wiegner, Viersen; Elmar Reinwald, Düsseldorf, both of Fed. Rep. of Germany

[73] Assignee: Henkel Kommanditgesellschaft auf Aktien, Düsseldorf, Fed. Rep. of Germany

[21] Appl. No.: 319,914

[22] Filed: Nov. 10, 1981

[30] Foreign Application Priority Data

May 29, 1981 [DE] Fed. Rep. of Germany ....... 3121364

[51] Int. Cl.$^3$ ............................................. A61F 15/00
[52] U.S. Cl. ........................................ 604/14; 604/18
[58] Field of Search ................... 128/263, 270, 285; 604/11–12, 14–16, 18

[56] References Cited

U.S. PATENT DOCUMENTS

| | | | |
|---|---|---|---|
| 2,509,241 | 5/1950 | Mende | 128/263 |
| 3,419,005 | 12/1968 | Lewing | 128/263 |
| 3,433,225 | 3/1969 | Voss et al. | 128/263 |
| 3,581,744 | 6/1971 | Voss et al. | 128/263 |
| 3,628,533 | 12/1971 | Loyer | 128/263 |
| 3,645,263 | 2/1972 | Bates | 128/263 |
| 3,724,462 | 4/1973 | Hanke | 128/263 |
| 3,760,808 | 9/1973 | Bleuer | 128/263 |
| 3,895,634 | 7/1975 | Berger et al. | 604/14 |
| 3,911,917 | 10/1975 | Hanke | 128/263 |
| 4,099,976 | 7/1978 | Kraskin et al. | 128/263 |

*Primary Examiner*—C. Fred Rosenbaum

*Attorney, Agent, or Firm*—Hammond & Littell, Weissenberger and Muserlian

[57] ABSTRACT

This invention relates to a tampon applicator. More particularly, this invention relates to an application system for hygienic introduction of a tampon which comprises a substantially cylindrical outer sleeve, a substantially cylindrical inner sleeve displaceable therein having an outer diameter substantially the same as the inner diameter of the outer sleeve and a flanged end, and a substantially cylindrical tampon, wherein (a) the front end of the outer sleeve is a conically rounded lamellar shutter means consisting of a ring of tulip-shaped lamellae abutting a circumferential groove acting as a hinge means, the shutter means being normally closed and opening during ejection of the tampon; (b) the outer sleeve consists of a high-gloss, plastic-coated paper, said paper being coated on the outer surface and said coated paper being readily water degradable or water dispersible; (c) the inner sleeve is comprised of water degradable or water dispersible paper; (d) the inner surface of the outer sleeve and the outer surface of the inner sleeve have co-efficients of friction such that they do not readily slide without applied pressure but on application of slight manual pressure readily slide, thus facilitating the opening of the lamellar shutter means and ejection of the tampon; (e) the outer sleeve has a grip in the form of a scoring; (f) said inner sleeve has substantially the same length as the outer sleeve; and (g) the outer sleeve, inner sleeve, and tampon form with the closed lamellar shutter means at the front end of the tampon a substantially closed system.

4 Claims, 3 Drawing Figures

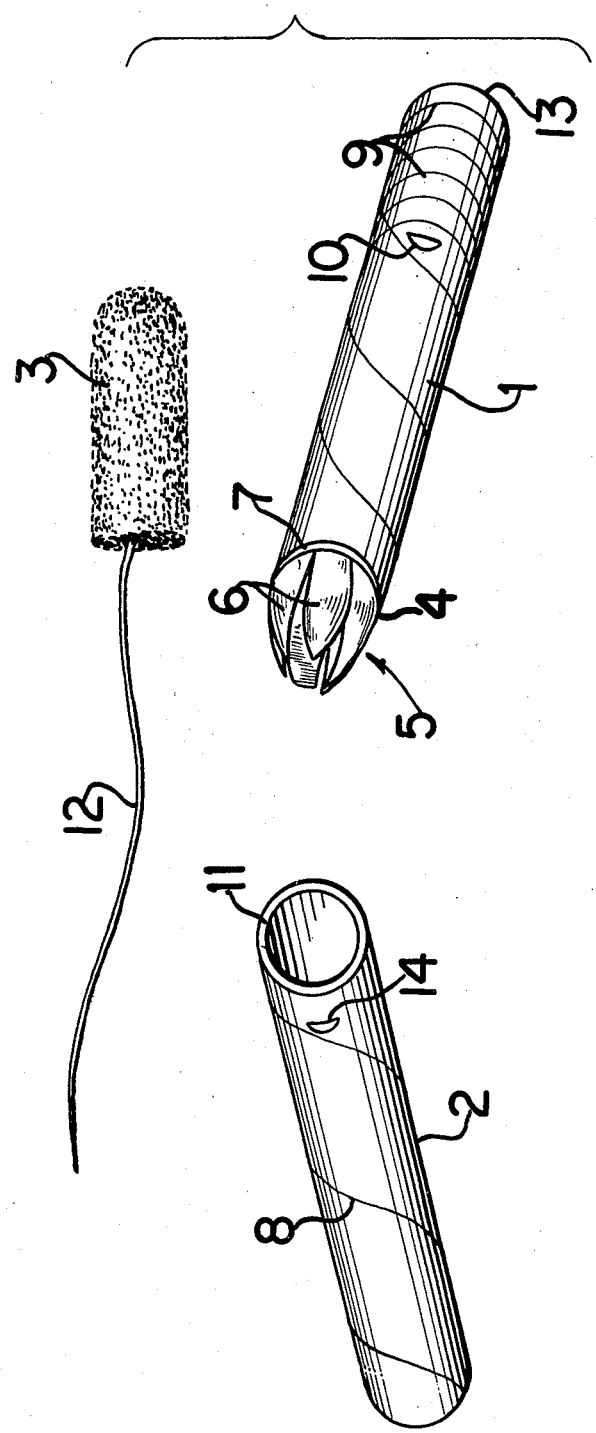

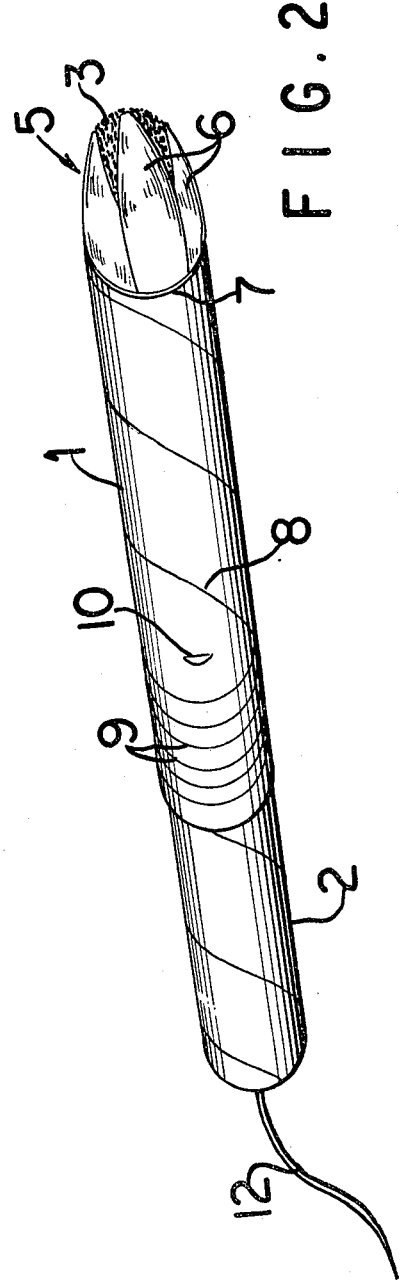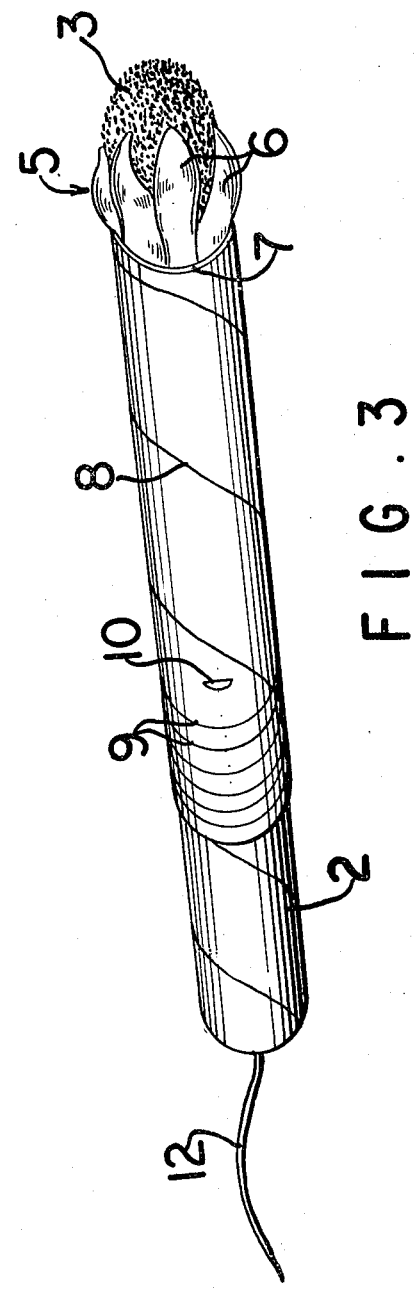

TAMPON APPLICATOR

FIELD OF THE INVENTION

This invention relates to a tampon applicator. More particularly, this invention relates to an application for the hygienic introduction of a tampon during the menstrual cycle of a woman, the applicator having a substantially cylindrical sleeve to facilitate introduction and a displaceable inner sleeve for ejecting the tampon.

BACKGROUND OF THE INVENTION

An applicator-tampon, such as, for example, that described in German published application (DE-AS) No. 20 43 293, has the advantage of clean and hygienic introduction, as compared to that of a digital tampon. Such applicator-tampons must meet a number of gynecological, environmental, and marketing criteria which are partly contradictory. To avoid injury to tissues during introduction into the vagina, the applicator material should have a smooth surface. For reasons concerning sensual impact, however, the surface should not be cold, hard, or plastic. In addition, the applicator should be water degradable or water dispersible, so that it can be disposed in a toilet. To also avoid injury to tissues during introduction of the tampon, the front end should be conically rounded. However, it should be possible to easily open this end during ejection of the tampon so that the expulsion pressure does not exceed 500 grams during ejection. On the other hand, the front end must not open so easily that the tampon would drop out from the sleeve and become contaminated before use. The applicator should thus form a substantially closed system. Finally, despite the requirement for a smooth surface, a grip would be advantageous for easy handling of the applicator.

OBJECTS OF THE INVENTION

It is an object of this invention to provide an applicator for a tampon.

It is also an object of the invention to provide an applicator system which meets the gynecological, environmental, and marketing criteria discussed above.

It is a further object of the invention to provide an applicator system comprising a substantially cylindrical outer sleeve, a substantially cylindrical inner sleeve displaceable therein having an outer diameter substantially the same as the inner diameter of the outer sleeve and a flanged end, and a substantially cylindrical tampon, wherein (a) the front end of the outer sleeve is a conically rounded lamellar shutter means consisting of a ring of tulip-shaped lamellae abutting a circumferential groove acting as a hinge means, the shutter means being normally closed and opening during ejection of the tampon; (b) the outer sleeve consists of a high-gloss, plastic-coated paper, said paper being coated on the outer surface and said coated paper being readily water degradable or water dispersible; (c) the inner sleeve is comprised of water degradable or water dispersible paper; (d) the inner surface of the outer sleeve and the outer surface of the inner sleeve have co-efficients of friction such that they do not readily slide without applied pressure but on application of slight manual pressure readily slide, thus facilitating the opening of the lamellar shutter means and ejection of the tampon; (e) the outer sleeve has a grip in the form of a scoring; (f) said inner sleeve has substantially the same length as the outer sleeve; and (g) the outer sleeve, inner sleeve, and tampon form with the closed lamellar shutter means at the front end of the tampon a substantially closed system.

These and other objects of the invention will become more apparent in the discussion below.

BRIEF DESCRIPTION OF THE DRAWINGS

FIG. 1 represents the three parts of the invention in disassembled form;

FIG. 2 represents the embodiment of the invention shown in FIG. 1 in assembled form; and FIG. 3 represents a view of an embodiment of the invention with the tampon partly ejected.

DETAILED DESCRIPTION OF THE INVENTION

Applicants have developed an applicator system which meets the above-mentioned gynecological, environmental, and marketing criteria in an optimum fashion. According to their invention, an applicator system comprises a substantially cylindrical outer sleeve, a substantially cylindrical inner sleeve displaceable therein having an outer diameter substantially the same as the inner diameter of the outer sleeve and a flanged end, and a substantially cylindrical tampon, wherein (a) the front end of the outer sleeve is a conically rounded lamellar shutter means consisting of a ring of tulip-shaped lamellae abutting a circumferential groove acting as a hinge means, the shutter means being normally closed and opening during ejection of the tampon; (b) the outer sleeve consists of a high-gloss, plastic-coated paper, said paper being coated on the outer surface and said coated paper being readily water degradable or water dispersible; (c) the inner sleeve is comprised of water degradable or water dispersible paper; (d) the inner surface of the outer sleeve and the outer surface of the inner sleeve have co-efficients of friction such that they do not readily slide without applied pressure but on application of slight manual pressure readily slide, thus facilitating the opening of the lamellar shutter means and ejection of the tampon; (e) the outer sleeve has a grip in the form of a scoring; (f) said inner sleeve has substantially the same length as the outer sleeve; and (g) the outer sleeve, inner sleeve, and tampon form with the closed lamellar shutter means at the front end of the tampon a substantially closed system.

The above-mentioned requirements are all met at the same time by the material, shape, and functional design, as well as by the ease of manufacture, of the applicator system according to the invention. The outer sleeve is comprised of a high-gloss paper which can be coated on the outer surface with plastic and printed in colors. The plastic coat can be applied to the paper by means of an extruder over a slot die. The requirements for the plastic coatings are fairly non-specific. However, in accordance with other requirements of the invention, a coat thickness of from about 15 to 30 g/m$^2$ is preferred. The plastic should be a polymer which is degradable, dispersible, or even soluble in water. Polyethylene or polypropylene containing suitable wetting agents or other additives are preferred coating materials, but other materials, such as, for example, polyvinylidene chloride or a readily water soluble polymer such as polyvinyl alcohol, can also be used. The paper itself can be virtually any suitable wood pulp product which is rigid enough to function as a sleeve according to the invention and is then water degradable or water dispersible, so as to be disposable in, for example, a toilet. The inner sleeve can be comprised of the same paper or of a similar pulp product that is water degradable or water dispersible. Either the inner sleeve or the outer sleeve, or both, can comprise more than one layer of paper.

Due to the use of these materials, a number of advantages can be combined. First of all, the smooth surface of the plastic is combined with the natural appearance of paper. The material is completely flushable, easy to deform or cut, and, in contrast to purely plastic applicators, its cost depends on the price of the natural product wood. Coloring is effected simply by dyeing or printing the paper coat.

Other details of the invention can perhaps be better appreciated by making reference to the embodiments of the invention represented in the drawings. The applicator system represented in FIGS. 1 to 3 consists of outer sleeve 1, inner sleeve 2, and tampon 3. All three parts are substantially cylindrical. Front end 4 of outer sleeve 1, with a conically rounded shape, is designed as a lamellar shutter means 5 opening during ejection of tampon 3. Shutter means 5 comprises a ring of lamellae 6 which is substantially tulip-shaped in the closed stage (see FIG. 2), at the origin of which is provided a circumferential groove 7 which functions as a hinge during ejection or expulsion. Outer sleeve 1, which is usually wound in the same manner as inner sleeve 2—as can be seen from the helical line 8—has at its rear end 13 a grip means in the form of a scoring 9, as well as at least one notch 10 for positioning of outer sleeve 1 relative to inner sleeve 2. Tampon 3 is held at its front by lamellar shutter means 5 and at its back by inwardly flanged end 11 of inner sleeve 2. A pull thread 12 of tampon 3 extends through inner sleeve 2.

Prior to assembly, each notch 10, which comprises a small flap having a substantially semi-circular shape, is co-extensive with the surface of outer cylinder 1. During assembly, described below, the flap is forced toward the interior of the outer sleeve, where it acts to engage inner sleeve 2 and to assist in preventing inner sleeve 2 from disengaging from outer sleeve 1, which would allow the tampon 3 to fall out. Similarly, inner sleeve 2 may have at least one notch 14, which comprises a small flap having a substantially semi-circular shape. Notch 14 is at some point co-extensive with the surface of inner sleeve 2 but is forced outward, either before or during assembly. During application of the tampon, inner sleeve 2 passes into the interior of outer sleeve until each notch 14 contacts the rear or lower portion 13 of outer sleeve 1. Preferably each notch 14 is positioned on inner sleeve 2 so that when the notch 14 contacts the rear or lower portion 13, flanged end 11 is approximately level with the lamellar shutter means 5.

By use of the above-described material, an extremely functional design can be obtained. This can be seen particularly from the example of a round head of the applicator designed as a lamellar shutter 5. In the manufacture of the round head, parts are so punched out at the front end of outer sleeve 1, as it will be described below, that the ring or lamellae 6 is obtained. This ring can be formed to a tulip-shaped shutter by suitable selection of the material properties of the paper, which can be multi-layered if necessary.

To make sure that the tulip-shaped lamellar shutter 5 can readily open during the ejection of tampon 3, a circumferential groove 7 is provided in outer sleeve 1 at the base of lamellae 6. This groove 7 acts as a hinge on lamellae 6 in such a way that, with an easily opening lamellar shutter 5, tampon 3 can be readily ejected at a low expulsion pressure.

The ejection of tampon 3 is also facilitated by careful adjustment, or "tuning", of the co-efficients of friction of the inner surface or coat of outer sleeve 1 and outer surface or coat of inner sleeve 2. Tuning of the co-efficients of friction independent of most other requirements and functions is possible because the sleeve wall can be composed of several layers. Consequently, it is possible to obtain very different material properties and meet different requirements on the outside and inside of sleeves 1 and 2, respectively, independent of each other. The object of the tuning is that inner sleeve 1 and outer sleeve 2 should not readily slide past one another without application of pressure. However, upon application of slight manual pressure the sleeves should readily slide to facilitate opening of the shutter means 5 and ejection of the tampon 3.

The applicator according to the invention can be designed as a closed system, since the tampon is held at the front end by lamellar shutter 5 and on the back by flange 11 of inner sleeve 2. Inner sleeve 2 and outer sleeve 1 are designed so that because of (1) the similarity of the outer diameter of inner sleeve 2 and the inner diameter of outer sleeve 1 and (2) the respective co-efficients of friction, inner sleeve 2 does not readily slide within outer sleeve 1 in the absence of applied pressure. In addition, inner sleeve 2 is also positioned with regard to outer sleeve 1 by at least one notch 10. The resistance provided by the coefficients of friction and each notch 10 is overcome during ejection of the tampon.

The new applicator can be brought—after separate winding—together with the tampon to its final form on one and the same machine. In one embodiment, the prefabricated sleeve is pushed over a heated inner mandrel, and several such mandrels can be arranged on a timed rotating disk. In this embodiment a punch moves at first toward this mandrel and cuts out segments in such a way that a ring of lamellae remains. In the next station, the corresponding scorings 7 and 9 are provided at the base of lamellae 6 and at the opposite end of outer sleeve 1. Finally lamellae 6 are flanged in the last station on the disk by means of a heated tool to the above-described tulip-shaped lamellar shutter 5. The finished outer sleeve 1 is inserted into a drum in which outer sleeve 1, tampon 3, and inner sleeve 2 are arranged in series. The three elements can be pushed one into the other by means of a plunger, and the unit can be held together by at least one notch 10 created by means of a needle.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An applicator system for hygienic introduction of a tampon which comprises a substantially cylindrical outer sleeve, a substantially cylindrical inner sleeve displaceable therein having an outer diameter substantially the same as the inner diameter of the outer sleeve and a flanged end, and a substantially cylindrical tampon, wherein (a) the front end of the outer sleeve is a conically rounded lamellar shutter means consisting of a ring of tulip-shaped, folded, individual lamellae abutting a circumferential groove, the shutter means being normally closed and opening during ejection of the tampon, the circumferential groove acting as a hinge means; (b) the outer sleeve consists of a high-gloss, plastic-coated paper, said paper being coated on the outer surface and said coated paper being readily water degradable or water dispersible; (c) the inner sleeve is comprised of water degradable or water dispersible paper; (d) the inner surface of the outer sleeve and the outer surface of the inner sleeve have co-efficients of friction such that they do not readily slide without applied pressure but on application of slight manual pressure readily slide, thus facilitating the opening of the lamellar shutter means and ejection of the tampon; (e) the outer sleeve has a grip in the form of a scoring; (f) said inner sleeve has substantially the same length as the outer sleeve; and (g) the outer sleeve, inner sleeve, and tampon form with the closed lamellar shutter means at the front end of the tampon a substantially closed system.

2. The applicator system of claim 1, wherein the plastic coating of the outer sleeve comprises polyethylene, polypropylene, polyvinylidene chloride, or polyvinyl alcohol.

3. The applicator system of claim 1, wherein the inner sleeve is positioned within the outer sleeve by one or more notches.

4. An application system for hygienic introduction of a tampon which comprises a substantially cylindrical outer sleeve, a substantially cylindrical inner sleeve displaceable therein having an outer diameter substantially the same as the inner diameter of the outer sleeve and a flanged end, and a substantially cylindrical tampon, wherein (a) the front end of the outer sleeve is a conically rounded lamellar shutter means consisting of a ring of tulip-shaped, folded, individual lamellae abutting a circumferential groove, the shutter means being normally closed and opening during ejection of the tampon, the circumferential groove acting as a hinge means; (b) the outer sleeve consists of a high-gloss, plastic-coated paper, said paper being coated on the outer surface with from 15 to 30 $g/m^2$ of a polymeric material selected from the group consisting of polyethylene, polypropylene, polyvinylidene chloride, and polyvinyl alcohol and said coated paper being readily water degradable or water dispersible; (c) the inner sleeve is comprised of water degradable or water dispersible paper; (d) the inner surface of the outer sleeve and the outer surface of the inner sleeve has co-efficients of friction such that they do not readily slide without applied pressure but on application of slight manual pressure readily slide, thus facilitating the opening of the lamellar shutter means and ejection of the tampon; (e) the outer sleeve has a grip in the form of a scoring; (f) said inner sleeve has substantially the same length as the outer sleeve; (g) the inner sleeve is positioned within the outer sleeve by one or more notches; and (h) the outer sleeve, inner sleeve, and tampon form with the closed lamellar shutter means at the front end of the tampon a substantially closed system.

* * * * *

UNITED STATES PATENT AND TRADEMARK OFFICE
CERTIFICATE OF CORRECTION

PATENT NO. : 4,412,833
DATED : November 1, 1983
INVENTOR(S) : GEORG WIEGNER et al.

It is certified that error appears in the above-identified patent and that said Letters Patent is hereby corrected as shown below:

Column 3, line 48: "outer sleeve" should read

--outer sleeve 1 --

Signed and Sealed this

Tenth Day of April 1984

[SEAL]

Attest:

GERALD J. MOSSINGHOFF

Attesting Officer     Commissioner of Patents and Trademarks